(12) United States Patent
Kuo

(10) Patent No.: US 6,904,619 B2
(45) Date of Patent: Jun. 14, 2005

(54) ADHESION OF DIVING GOGGLE LENSES

(76) Inventor: Tzong-Fuh Kuo, No. 21, Alley 5, Lane 49, How Gaang 1st Rd., Hsin Juang City, Taipei Hsien (TW)

(*) Notice: Subject to any disclaimer, the term of this patent is extended or adjusted under 35 U.S.C. 154(b) by 176 days.

(21) Appl. No.: 10/337,772

(22) Filed: Jan. 8, 2003

(65) Prior Publication Data
US 2004/0128746 A1 Jul. 8, 2004

(51) Int. Cl.[7] .................................................. A61F 9/02
(52) U.S. Cl. ........................................................ 2/426
(58) Field of Search ............................ 2/5, 6.3, 6.4, 6.5, 2/6.7, 15, 426, 428, 440, 454

(56) References Cited

U.S. PATENT DOCUMENTS 5,553,331 A * 9/1996 Gentile ........................ 2/430
5,603,124 A * 2/1997 Garofalo ...................... 2/428

* cited by examiner

Primary Examiner—John Calert
Assistant Examiner—Brian Kauffman
(74) Attorney, Agent, or Firm—Bacon & Thomas

(57) ABSTRACT

A device formed of adhesion of diving goggle lenses. The device includes a goggle frame, a mask, a front lens and a lateral lens. The front and lateral lens are fixedly adhered by an L-shaped or T-shaped leak-proof gasket of a soft material with high diaphaneity so as to prevent a crack or water leakage between the lenses due to a bump or impact.

4 Claims, 5 Drawing Sheets

ADHESION OF DIVING GOGGLE LENSES

BACKGROUND OF THE INVENTION

1) Field of the Invention

The present invention relates to an adhesion of diving goggle lenses, more particularly to an adhesion between a front lens and a lateral lens of the diving goggle that uses a leak-proof gasket of a soft material with high diaphaneity to provide the adhesion with elasticity so as to prevent crack formation or water leakage due to a bump or impact.

2) Description of the Prior Art

Accordingly, the viewing angle provided by a conventional diving goggle with single window (single lens) or dual windows (dual lenses) is far narrower than that of a naked eye. As indicated in FIG. 7, lateral windows on the left and right sides of an available three-window or four-window diving goggle are either unitarily molded by transparent material and a frame body or including two small pieces of planar glass inserted on the left and right sides. The above-mentioned diving goggle with three or four windows is actually confined by the frame rims mounted on the front, left and right windows such that the view thereof is limited and the effect is not desired.

In order to improve the abovementioned diving goggle with three or four windows, a diving goggle with a wide view was developed, as indicated in FIG. 8. Although such device is capable of providing a wide view, the front lens (21) and the lateral lens (22) are adhered by glue. The lens on the beveled plane is not easy for adhering and subject to formation of cracks, detachment or water leakage at the glued area due to a bump or impact occurring at the sea bottom.

SUMMARY OF THE INVENTION

The primary objective of the present invention is to adhere a leak-proof gasket of a soft material with high diaphaneity at the connecting area between a front lens and a lateral lens of a diving goggle such that the adhered areas of the two lenses are elastic so as to prevent crack formation or water leakage due to a bump.

To enable a further understanding of the technical contents of the present invention, the brief description of the drawings is followed by the detailed description of a preferred embodiment.

DETAILED DESCRIPTION OF THE PREFERRED EMBODIMENTS

Figure 1:
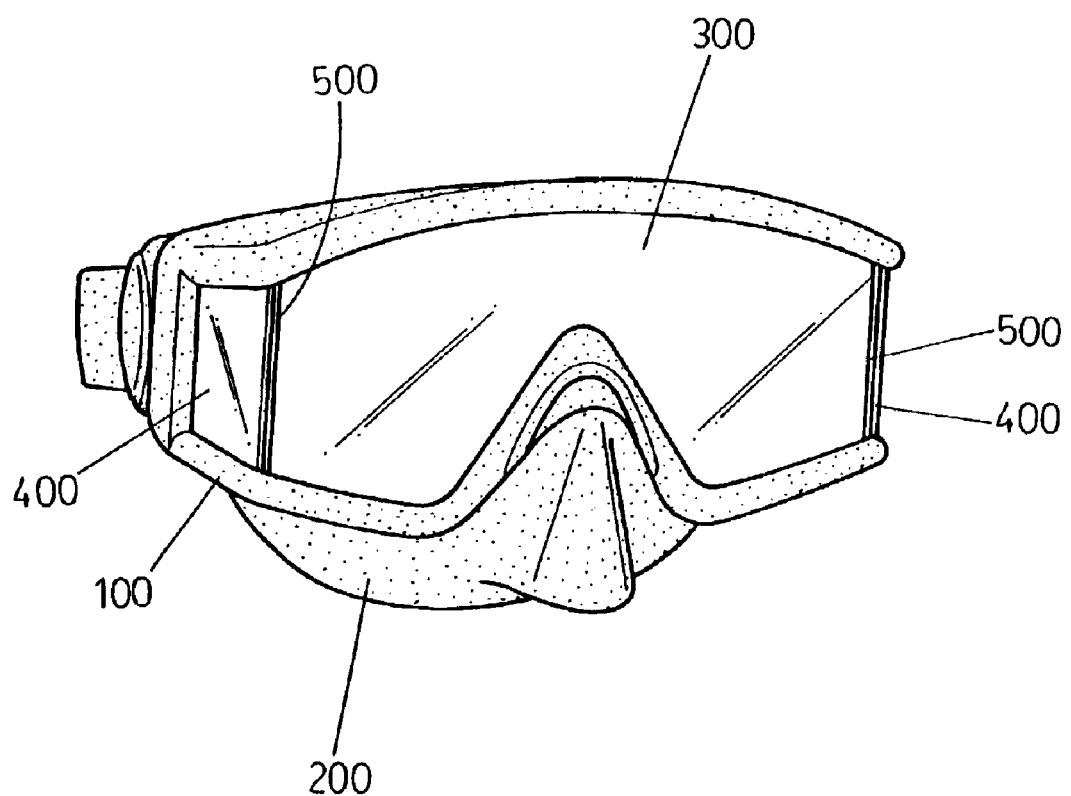
FIG. 1 a perspective view drawing of the present invention.
Figure 2:
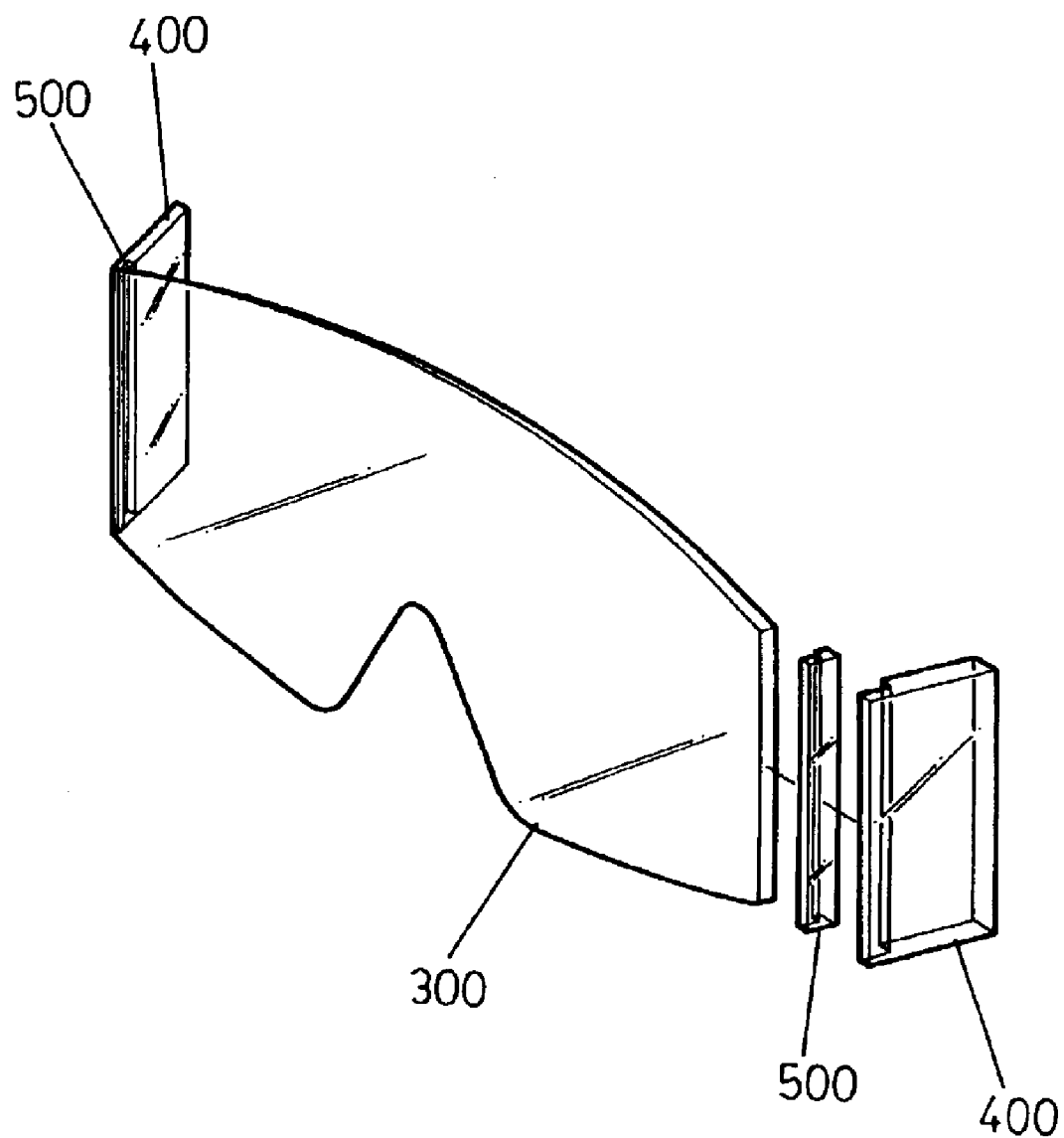
FIG. 2 is a partially exploded view of the lenses of the present invention.
Figures 3, 4:
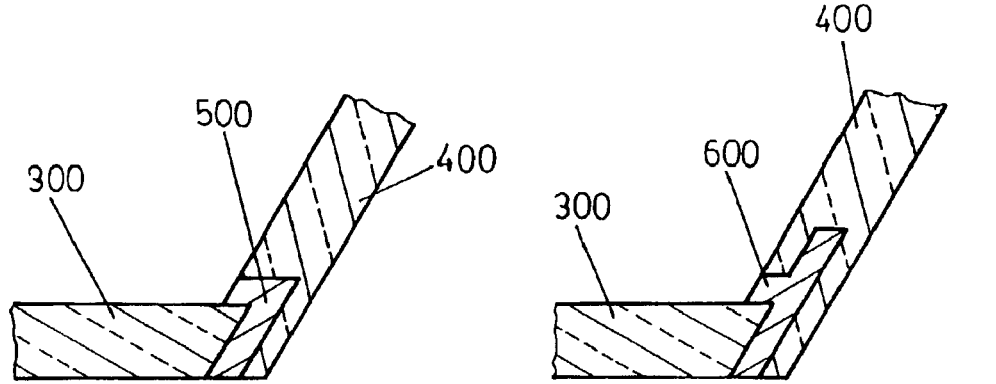
FIG. 3 is a partial cross-sectional view of the lenses of the present invention.
FIG. 4 is a first partial cross-sectional view of the lenses of an exemplary embodiment of the present invention.

With reference to FIGS. 1 to 3, the present invention comprises a goggle frame (100), a mask (200), a front lens (300) and a lateral lens (400). The goggle frame (100) is disposed at the front aspects of the lenses (300, 400) and the mask (200) is disposed at the rear aspects of the lenses (300, 400). The present invention is characterized in that a soft leak-proof gasket (500) is fixedly adhered between the front lens (300) and the lateral lens (400). The leak-proof gasket (500) has high diaphaneity to hold a contact plane between the two rigid front and lateral lenses (300, 400) and therefore, no crack occurs even after a bump or impact and no water leakage occurs. The leak-proof effect improves when the sea water pressure increases.

Referring to FIGS. 3 and 4, the front lens (300) and the lateral lens (400) connect to form a beveling plane; the leak-proof gaskets (500, 600) are in an L-shape or a T-shape.

Figures 5, 6:
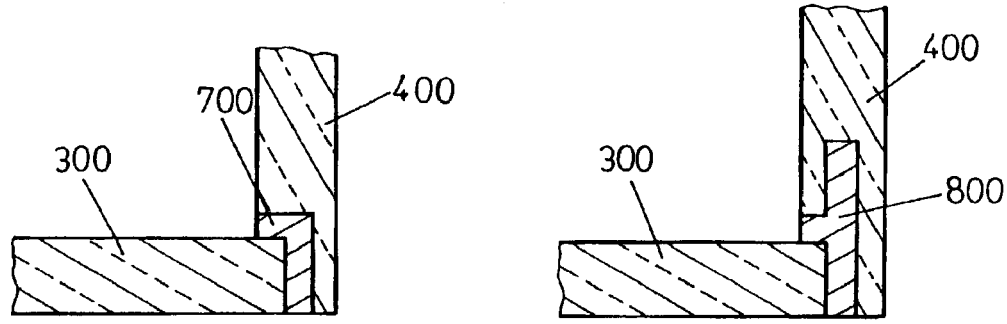
FIG. 5 is a second partial cross-sectional view of the lenses of an exemplary embodiment of the present invention.
FIG. 6 is a third partial cross-sectional view of the lenses of an exemplary embodiment of the present invention.
Figure 7:
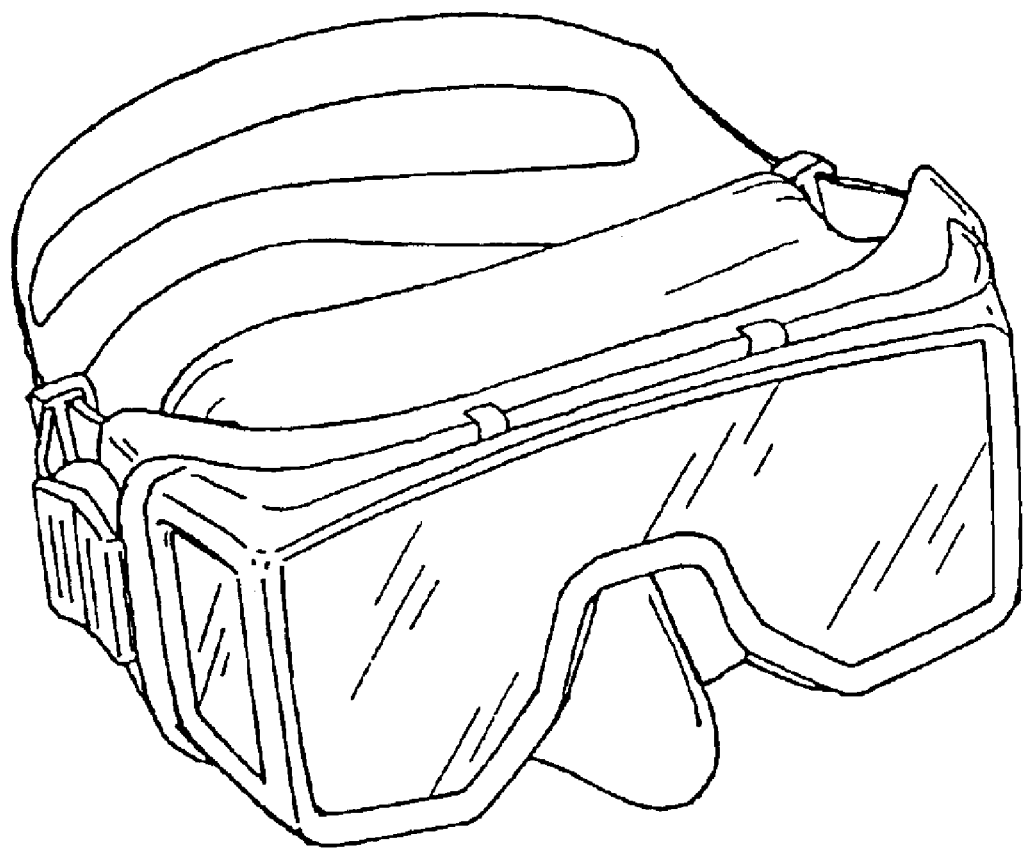
FIG. 7 is a perspective view of a conventional product.
Figure 8:
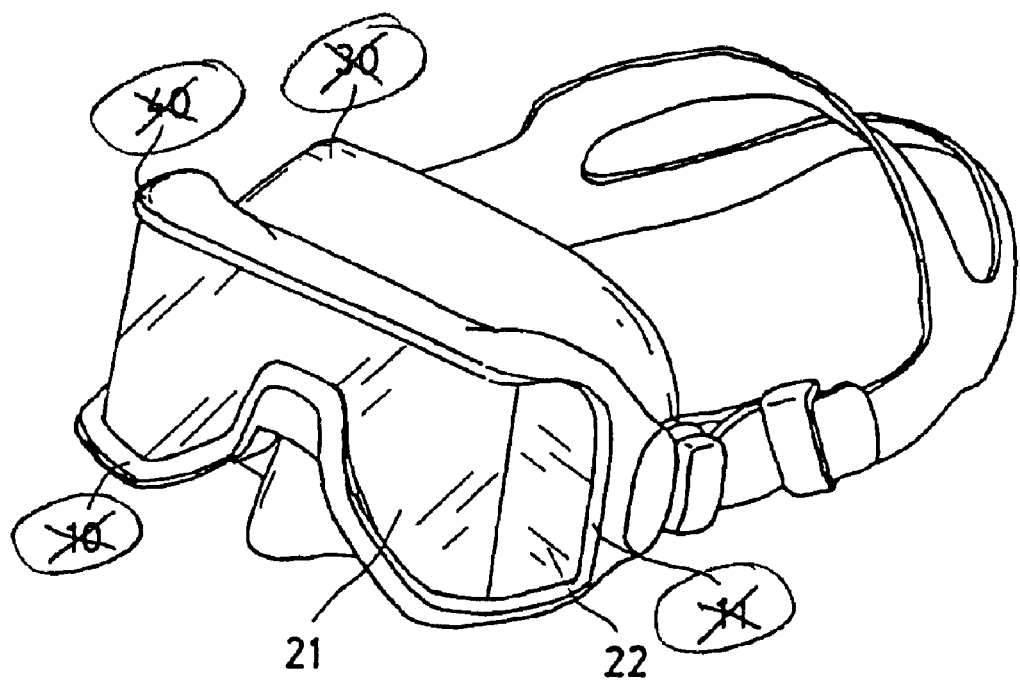
FIG. 8 is a perspective view of another conventional product.

Referring to FIGS. 5 and 6, the front lens (300) and the lateral lens (400) connect to form a vertical plane; the leak-proof gaskets (700, 800) are in an L-shape or a T-shape.

In summation of the abovementioned, the present invention uses the soft leak-proof gasket to fixedly adhere the connection between the front lens and the lateral lens of the diving goggle; the leak-proof gasket has preferred elasticity for preventing the lenses from cracking or leaking due to a bump.

It is of course to be understood that the embodiment described herein is merely illustrative of the principles of the invention and that a wide variety of modifications thereto may be effected by persons skilled in the art without departing from the spirit and scope of the invention as set forth in the following claims.

What is claimed is:

1. A diving goggle comprising:

a goggle frame, a mask, a front lens and a lateral lens;

the goggle frame is disposed at front aspects of the front and lateral lenses while the mask is disposed at rear aspects of the front and lateral lenses;

a soft leak-proof gasket is fixedly adhered between the front lens and the lateral lens; and the leak-proof gasket is a structure of high diaphaneity.

2. The adhesion of diving goggle lenses according to claim 1, wherein the front lens and the lateral lens connect to form a bevel plane or a vertical plane.

3. A diving goggle comprising:

a goggle frame, a mask, a front lens and a lateral lens;

the goggle frame is disposed at front aspects of the front and lateral lenses while the mask is disposed at rear aspects of the front and lateral lenses;

a soft leak-proof gasket is fixedly adhered between the front lens and the lateral lens; and the leak-proof gasket is in an L-shape or a T-shape.

4. The adhesion of diving goggle lenses according to claim 3, wherein the front lens and the lateral lens connect to form a bevel plane or a vertical plane.

* * * * *